United States Patent
Imamoto et al.

(10) Patent No.: US 7,534,920 B2
(45) Date of Patent: May 19, 2009

(54) OPTICALLY-ACTIVE BIS(ALKYNYLPHOSPHINO) ETHANE-BORANE DERIVATIVE AND PROCESS FOR PRODUCING THE SAME

(75) Inventors: Tsuneo Imamoto, Chiba (JP); Kazuhiro Yoshida, Chiba (JP); Youichi Saitoh, Chiba (JP); Aya Koide, Chiba (JP)

(73) Assignees: Nippon Chemical Industrial Co., Ltd., Tokyo (JP); National University Corporation Chiba University, Chiba-shi (JP)

( * ) Notice: Subject to any disclaimer, the term of this patent is extended or adjusted under 35 U.S.C. 154(b) by 0 days.

(21) Appl. No.: 12/073,415

(22) Filed: Mar. 5, 2008

(65) Prior Publication Data

US 2008/0221362 A1    Sep. 11, 2008

(30) Foreign Application Priority Data

Mar. 9, 2007    (JP)    ............................. 2007-060784

(51) Int. Cl.
    *C07F 9/02*    (2006.01)
(52) U.S. Cl. ....................................................... 568/10
(58) Field of Classification Search ................... 568/10
    See application file for complete search history.

(56) References Cited

FOREIGN PATENT DOCUMENTS

EP    0997470    5/2000
JP    11-080179    3/1999

OTHER PUBLICATIONS

Schuman et al., {Novel synthesis of borane complexes of cyclic phosphanes using ruthenium-catalyzed olefin metathesis, Angewandte Chemie, International Edition (2000), 39(14), 2491-2493}.*

Cedric Genet et al., "Catalytic Asymmetric Synthesis of Ferrocenes and P-Stereogenic Bisphosphines," J. Am. Chem. Soc., vol. 128, No. 29, pp. 9336-9337, Jul. 26, 2006.

* cited by examiner

*Primary Examiner*—Elvis O Price
*Assistant Examiner*—Chukwuma O Nwaonicha
(74) *Attorney, Agent, or Firm*—Edwards Angell Palmer & Dodge LLP

(57) ABSTRACT

An optically-active bis(alkynylphosphino)ethane-borane derivative represented by formula (1):

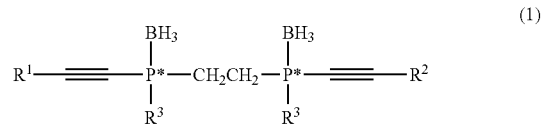

wherein $R^1$ and $R^2$, which may be the same or different, each represent an alkyl group, a phenyl group, an alkyl-silyl group or a hydrogen atom; $R^3$ represents a branched alkyl group, an alicyclic hydrocarbon group or an aromatic hydrocarbon group; and the asterisk * indicates an optically-active site.

The derivative (1) is prepared by bromination of, e.g., an (S)-t-butylmethylphosphine-borane, reaction with an alkynyl lithium, deprotonation, followed by oxidative coupling. Deprotection of the derivative (1) by deboranation gives an optically-active bis(alkynylphosphino)ethane derivative useful as a ligand providing an asymmetric catalyst for catalytic asymmetric synthesis. The asymmetric catalyst having the ligand exhibits high selectivity and catalyst activity.

5 Claims, No Drawings

OPTICALLY-ACTIVE BIS(ALKYNYLPHOSPHINO) ETHANE-BORANE DERIVATIVE AND PROCESS FOR PRODUCING THE SAME

FIELD OF THE INVENTION

This invention relates to an optically-active bis(alkynylphosphino)ethane-borane derivative and a process for producing the same. The bis(alkynylphosphino)ethane-borane derivative provides a bis(alkynylphosphino)-ethane derivative, which is useful as a ligand of a metal complex as an asymmetric catalyst for asymmetric syntheses.

BACKGROUND OF THE INVENTION

Catalytic asymmetric synthesis is known useful as a process of producing optically-active compounds including agricultural chemicals and pharmaceuticals. A catalytic asymmetric synthesis reaction using an optically-active catalyst (hereinafter referred to as "asymmetric catalyst") has a great deal of potential in industry because it enables synthesis of large quantities of an optically-active compound using a very small amount of the asymmetric catalyst. Known useful asymmetric catalysts and asymmetric ligands constituting the catalysts are exemplified by an optically-active bisphosphinomethane represented by formula (5) below and a rhodium complex having this (see EP0997470A1).

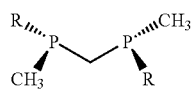

(5)

Also known are a compound represented by formula (6) below, which is different in part from but structurally similar to the compound of EP0997470A1, and a compound obtained therefrom by deboranation (see JP 11-80179A and J.

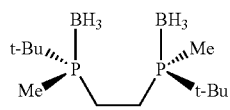

(6)

Am. Chem. Soc., vol. 128, No. 29, pp 9336-9337).

For the purpose of developing asymmetric catalysts with improved performance, a vast number of optically-active diphosphine ligands have been proposed, including the above-described compounds. However, there still remains room for improvements on selectivity, catalytic activity, and the like in applications to some kinds of substrates.

SUMMARY OF THE INVENTION

An object of the present invention is to provide a compound with improvements in various performance properties over conventional optically-active diphosphine ligands.

The present invention provides an optically-active bis(alkynylphosphino)-ethane-borane derivative represented by formula (1):

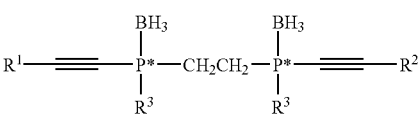

(1)

Wherein $R^1$ and $R^2$, which may be the same or different, each represent an alkyl group, a phenyl group, an alkylsilyl group or a hydrogen atom; $R^3$ represents a branched alkyl group, an alicyclic hydrocarbon group or an aromatic hydrocarbon group; and the asterisk * indicates an optically-active site.

The present invention also provides a process for producing the bis(alkynylphosphino)ethane-borane derivative. The process comprises the steps of:

brominating a t-butylmethylphosphine-borane represented by formula (2):

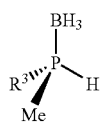

(2)

wherein $R^3$ is as defined above, to obtain a t-butylmethylbromophosphine-borane represented by formula (3):

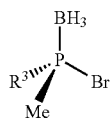

(3)

wherein $R^3$ is as defined above, causing an alkynyl lithium to react on the t-butylmethylbromophosphine-borane to obtain a configuration-inverted compound represented by formula (4):

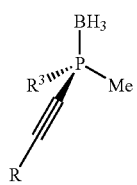

(4)

wherein R represents $R^1$ or $R^2$; and $R^3$ is as defined above, and deprotonating the compound of formula (4), followed by oxidative coupling.

DETAILED DESCRIPTION OF THE INVENTION

The compound represented by formula (1) is deprotected by deboranation in a usual manner to give a bis(alkynylphosphino)ethane derivative represented by formula (7):

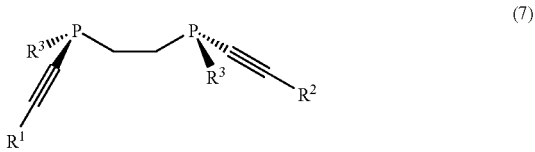

(7)

wherein $R^1$, $R^2$, and $R^3$ are as defined above.

The alkyl group as represented by $R^1$ or $R^2$ is substituted or unsubstituted and has a straight-chain, branched or cyclic structure. The alkyl group preferably contains 1 to 18, more preferably 1 to 8, carbon atoms. Examples of the alkyl group include methyl, ethyl, n-propyl, sec-propyl, n-butyl, sec-butyl, t-butyl, n-hexyl, sec-hexyl, n-heptyl, sec-heptyl, n-octyl, sec-octyl, t-octyl, n-decyl, n-dodecyl, n-hexadecyl, n-octadecyl, cyclohexyl, cyclooctyl, methylcyclohexyl, and the groups recited which are substituted with a functional group, e.g., a trimethylsilyl group, a nitro group, a hydroxyl group or a halogeno group.

The phenyl group as represented by $R^1$ or $R^2$ may be substituted or unsubstituted. Examples of the substituents of the hydrogen atom in the phenyl group include the above recited functional groups.

The alkylsilyl group as represented by $R^1$ or $R^2$ is represented by $R^a R^b R^c Si—$, wherein $R^a$, $R^b$, and $R^c$, which may be the same or different, each represent a substituted or unsubstituted and straight-chain, branched or cyclic alkyl group. All of $R^a$, $R^b$, and $R^c$ are preferably the same. The alkyl group as $R^a$, $R^b$, and $R^c$ preferably contains 1 to 8, more preferably 1 to 3, carbon atoms.

While $R^1$ and $R^2$ may be the same or different, they are preferably the same for ease of synthesis.

$R^3$ is a bulky group selected from a branched alkyl group, an alicyclic hydrocarbon group, and an aromatic hydrocarbon group. The branched alkyl group is exemplified by one having 3 to 20, preferably 3 to 8, carbon atoms. Examples of the branched alkyl group are isopropyl, t-butyl, 2,2-dimethylpropyl, and 1,1,3,3-tetramethylbutyl. Examples of the alicyclic hydrocarbon group include those having 3 to 20 carbon atoms, such as cyclopentyl, cyclohexyl, adamantyl, and norbornyl. Examples of the aromatic hydrocarbon group are phenyl, naphthyl, anthracenyl, and phenanthryl.

Although the alkynyl group in the bis(alkynylphosphino) ethane derivative of formula (7) is generally bulkier than the methyl group in the compound of JP 11-80179A supra, the carbon-carbon triple-bonded site of the former is considered narrow and less bulky than the methyl group because of the linearity of the bond formed by an sp-hybrid orbital of carbon. Additionally, seeing that an alkynyl group is an electron-withdrawing group, the phosphorus atom in the bis(alkynylphosphino)ethane derivative of formula (7) has a reduced electron density. Because of this reduction in electron density, the bis(alkynylphosphino)ethane derivative of formula (7) exhibits unique catalyst activity distinguishable from the compound disclosed in JP 11-80179A. It is also believed that the alkynyl group in the bis(alkynylphosphino)ethane derivative of formula (7) acts like an alkyne on the central metal element and substrate molecules in a catalytic asymmetric synthesis reaction to induce an interaction. The compound of JP 11-80179A supra never shows such a characteristic action.

In the present invention, it is preferred that $R^1$ and $R^2$ are the same and selected from a phenyl group, a t-butyl group, a methyl group, a triisopropylsilyl group, and a hydrogen atom; and it is preferred that $R^3$ is a t-butyl group or an adamantyl group. It is more preferred that $R^1$, $R^2$, and $R^3$ are selected from the respective preferred groups recited above.

A preferred process of preparing the compound of formula (1) is then described. The process starts with an (S)-t-butylmethylphosphine-borane of formula (2) described supra. The compound of formula (2) is prepared by a known process such as, e.g., disclosed in JP 2003-300988A, J. Org. Chem., vol. 65, No. 13, pp 4185-4188 (2000), and ibid, vol. 65, No. 6, pp. 1877-1880 (2000).

Bromination of the compound of formula (2) gives the t-butylmethylbromophosphine-borane of formula (3). Bromination is carried out by first lithiating the compound of formula (2), followed by bromination. Lithiation is conducted using an alkyl lithium, e.g., n-butyl lithium. Lithiation is performed preferably at a low temperature of –80° C. to –70° C. Lithiation is followed by bromination. Bromination is carried out using an alkyl bromide, e.g., dibromoethane, in a solvent, e.g., diethyl ether.

An alkynyl lithium is caused to react on the t-butylmethylbromophosphine-borane in situ, whereby bromine is displaced with the alkynyl group to give a compound of formula (4). The alkynyl lithium that can be used is exemplified by a compound represented by formula (8):

(8)

wherein R represents $R^1$ or $R^2$.

The alkynyl lithium is preferably added to the reaction system at a low temperature of –80° C. to –70° C. similarly to the reaction system for obtaining the compound of formula (3) from the compound of formula (2). The reaction system is then warmed to about room temperature. Surprisingly, the substitution reaction in this step is accompanied by nearly perfect configuration inversion. More specifically, an optical purity (ee) as high as 95% or even more is reached. As far as known to the present inventors, such a high optical purity in substitution with an alkene is achieved by the present invention for the first time.

The compound of formula (4) thus obtained is then subjected to deprotonation followed by oxidative coupling to afford a compound of formula (1). Deprotonation is achieved with an alkyl lithium such as sec-butyl lithium or t-butyl lithium. Deprotonation is preferably carried out at a low temperature of –80° C. to –70° C. The alkyl lithium is added to the reaction system in the form of a solution in an organic solvent, e.g., hexane. The Deprotonation reaction may be conducted in the co-presence of an amine, such as N,N,N',N'-tetramethylethylene-diamine.

The deprotonation is followed by in situ oxidative coupling. Oxidative coupling is carried out in a usual manner, for example, in the presence of copper (II) chloride. The bis (alkynylphosphino)ethane-borane derivative of formula (1) is thus obtained. When the coupling reaction is conducted using two kinds of the compounds of formula (4) different in R, a compound of formula (1) in which $R^1$ and $R^2$ are different is obtained. When, on the other hand, one kind of the compound of formula (4) is subjected to coupling reaction, a compound of formula (1) in which $R^1$ and $R^2$ are the same is obtained. A compound of formula (1) in which $R^1$ and $R^2$ are each a hydrogen atom is preferably obtained by once preparing a compound of formula (1) wherein $R^1$ or $R^2$ is an alkylsilyl group and then desilylating the resulting compound. A compound of formula (1) in which $R^1$ and $R^2$ are each a methyl group is preferably obtained by once preparing a compound of formula (1) wherein $R^1$ or $R^2$ is an alkylsilyl group, desilylating the resulting compound, followed by methylation.

When the bis(alkynylphosphino)ethane-borane derivative of formula (1) is used as a ligand of an asymmetric catalyst, the derivative is deprotected by deboranation. Deboranation is carried out using a secondary amine such as diethylamine or morpholine or a base such as 1,4-diazabicyclo[2.2.2]octane (DABCO) or triethylamine as reported in J. Am. Chem. Soc., 112, p 5244 (1990) and ibid, 121, p 1090 (1999). Deboranation may also be conducted in the presence of an excess of a tertiary amine as taught in ibid, 121, p 1090 (1999). A deboranation method using a strong acid such as tetrafluoroboric acid, trifluoroacetic acid, or trifluoromethanesulfonic acid is also known as described in Tetrahedron Lett., 35, 9319 (1994), J. Organomet. Chem., 621, 120 (2001), and J. Am. Chem. Soc., 120, p 1635 (1998). The method proposed in JP 2005-97131A is also useful, in which phosphine is released from phosphine borane in an alcohol solvent in the presence of Molecular Sieve.

The deboranation of the compound of formula (1) yields the bis(alkynylphosphino)ethane derivative of formula (7), which is coordinated to a metal such as rhodium or copper to provide an asymmetric catalyst. An asymmetric catalyst having the compound of formula (7) as a ligand is prepared in accordance with, for example, the process described in The Chemical Society of Japan (ed.), Jikken Kagaku Koza 4th Ed., Maruzen, vol. 18, pp. 327-353. For example, a rhodium complex is prepared by allowing the compound of formula (7) to react with[RhX(diene)$_2$], wherein X is halogen, $BF_4^-$, $PF_6^-$, $ClO_4^-$, etc.; and diene is a bidentate compound such as 1,5-cyclooctadiene or bicyclo[2,2,1]hepta-2,5-diene. The molar ratio of the compound of formula (7) to rhodium in the rhodium complex is preferably 1:1 to 2:1.

The asymmetric catalyst thus obtained is suited for use in various asymmetric synthesis reactions including, for example, asymmetric hydrogenation of an unsaturated carboxylic acid to produce an optically-active saturated carboxylic acid or an ester thereof and asymmetric hydrosilylation of a prochiral ketone to produce an optically-active secondary alcohol.

The present invention will now be illustrated in greater detail with reference to Examples. Unless otherwise noted, all the parts are by weight.

All the solvents used were dried and purified in accordance with standard procedures. NMR spectra were measured in a deuterium chloroform solvent using a spectrometer JMN-GXS-500 (500 MHz) or JMN-LA-400 (400 MHz) both available from JEOL Ltd. Chemical shifts were reported in delta ppm. Optical rotation was measured with a polarimeter DIP-370 from JASCO Corp. Optical purity (ee) was measured by HPLC on Chiralcel AD, OJ-H, OD-H, OB, and IA columns from Daicel Chemical Industries, Ltd. using a 2-propanol/hexane mixed solvent as a mobile phase. X-Ray crystallographic data were collected on an X-ray diffractometer SMART APEX II from Bruker AXS with an Mo—Kα radiation. In column chromatography, silica gel (60N for flash chromatography, from Kanto Chemical) was used.

EXAMPLE 1

(1-1) Synthesis of (S)-t-butylmethyl(phenylethynyl)phosphine-borane (4a)

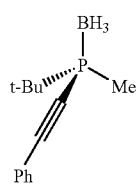

(4a)

In 60 ml of diethyl ether was dissolved 1.8 g (15.4 mmol) of (S)-t-butylmethylphosphine-borane (>99% ee), and 11.6 ml of a 1.60M hexane solution of n-butyl lithium (18.5 mmol) was added thereto at −78° C. in a nitrogen atmosphere, followed by aging by stirring for 15 minutes. To the reaction mixture was added dropwise 2.0 ml (23.1 mmol) of 1,2-dibromoethane, followed by aging by stirring at the same temperature. As a result, (R)-bromo-t-butylmethylphosphine-borane was obtained, which was used in the subsequent step without being isolated.

Two hours later, 30 ml of a diethyl ether solution containing 30.8 mmol of lithium phenylacetylide was added to the reaction mixture at −78° C. The temperature of the mixture was raised to room temperature, at which the mixture was aged while stirring for 1.5 hours. After the reaction, the reaction was quenched by addition of 1M hydrochloric acid. The reaction mixture was extracted three times with ethyl acetate. The organic layers were combined, washed successively with a saturated sodium hydrogencarbonate aqueous solution and a saturated sodium chloride aqueous solution, dried over anhydrous sodium sulfate, followed by filtration. The filtrate was concentrated under reduced pressure, and the residue was purified by silica gel column chromatography using a hexane/ethyl acetate (=5/1) mixed solvent as an eluent to give 2.8 g (12.8 mmol) of the title compound 4a as a white solid in a yield of 83% in 97% ee.

$^1$H-NMR (500 MHz, CDCl$_3$) δ 0.42-0.98 (m, 4H), 1.29 (d, J=15.6Hz, 9H), 1.51 (d, J=10.0 Hz, 3H), 7.33-7.37 (m, 2H), 7.41 (tt, J=15.3, 1.7 Hz, 1H), 7.50-7.52 (m, 2H).

$^{13}$C-NMR (125 MHz, CDCl$_3$) δ 8.37 (d, J=40 Hz), 24.96 (d, J=4 Hz), 29.03 (d, J=37 Hz), 79.42 (d, J=90 Hz), 106.00 (d, J=12 Hz), 120.77, 128.42, 130.01, 132.20.

$^{31}$P-NMR (162 MHz, CDCl$_3$) δ 17.95 (q, J=62 Hz).

[α]22D=0.97 (c=1.00, CHCl$_3$).

HPLC: Daicel Chiralcel OD-H, hexane/i-PrOH=199/1, flow rate=0.5 ml/min, Uv=254 nm, tR=11.9 min (R), tR=13.1 min (S).

(1-2) Synthesis of (S,S)-1,2-bis(boranato(t-butyl)phenylethynylphosphino)ethane (1a)

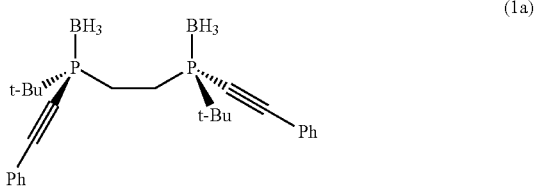

(1a)

In 13 ml of dried diethyl ether were dissolved 0.95 g (4.4 mmol) of 4a (94% ee) and 0.8 ml (5.2 mmol) of N,N,N',N'-tetramethylethylenediamine (TMEDA), and 5.2 ml of a 1.0M hexane solution of sec-butyl lithium (5.2 mmol) was added thereto at −78° C. in a nitrogen atmosphere, followed by aging by stirring at that temperature for 1 hour and then at −50° C. for 10 minutes. To the reaction mixture was added 1.5 g (11.0 mmol) of copper (II) chloride while vigorously stirring, and the reaction mixture was slowly warmed to room temperature. Two hours later, the reaction was quenched with a saturated aqueous solution of ammonium chloride. The reaction mixture was extracted three times with ethyl acetate. The organic layers were combined, washed with a saturated sodium chloride aqueous solution, dried over anhydrous sodium sulfate, and filtered. The filtrate was concentrated under reduced pressure, and the residue was purified by silica gel column chromatography (hexane/ethyl acetate=4/1) to give 0.69 g (1.6 mmol) of the title compound 1a as a white solid in a yield of 73% in >99% ee.

$^1$H-NMR (500 MHz, CDCl$_3$) δ 0.57-0.80 (m, 6H), 1.33 (d, J=15.6 Hz, 18H), 2.13-2.28 (m, 4H), 7.29-7.32 (m, 4H), 7.41 (tt, J=15.0 Hz, 2.5 Hz, 2H), 7.46-7.47 (m, 4H).

$^{13}$C-NMR (100 MHz, CDCl$_3$) δ 17.01 (d, J=34 Hz), 25.30 (t, J=3 Hz), 30.11 (d, J=36 Hz), 77.88 (d, J=88 Hz), 107.38 (t, J=12 Hz), 120.39 (t, J=3 Hz), 128.48, 130.22, 132.24.

$^{31}$P-NMR (162 MHz, CDCl$_3$) δ 29.62 (d, J=15 Hz).

[α]22D=111.1 (c=1.00, CHCl$_3$).

(1-3) Synthesis of (S,S)-1,2-bis((t-butyl)phenylethynylphosphino)ethane (7a)

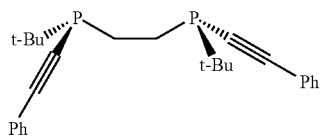

(7a)

A solution of 36 mg (0.084 mmol) of 1a and 56 mg (0.51 mmol) of 1,4-diazabicyclo[2.2.2]octane in 0.5 ml of THF was stirred at 60° C. in a nitrogen atmosphere for 1 hour, followed by concentration under reduced pressure. The residue was purified by flash column chromatography (diethyl ether) in a nitrogen atmosphere to afford 32 mg (0.079 mmol) of the title compound 7a in a yield of 94% in >99% ee.

EXAMPLE 2

(2-1) Synthesis of (S)-t-butyl(t-butylethynyl)methylphosphine-borane (4b)

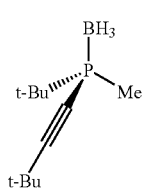

(4b)

The title compound 4b was obtained in the same manner as in Example 1, except for replacing lithium phenylacetylide with lithium t-butylacetylide. The yield was 0.57 g (2.9 mmol, 82%) with 97% ee.

$^1$H-NMR (400 MHz, CDCl$_3$) δ 0.23-0.89 (m, 3H), 1.21 (d, J=15.1 Hz, 9H), 1.27 (s, 9H), 1.38 (d, J=10.0 Hz, 3H).

$^{13}$C-NMR (100 MHz, CDCl$_3$) δ 0, 8.54 (d, J=40 Hz), 24.77 (d, J=3 Hz), 28.62 (d, J=35 Hz), 30.20 (d, J=2 Hz), 68.70 (d, J=95 Hz), 116.79 (d, J=10 Hz).

$^{31}$P-NMR (162 NHz, CDCl$_3$) δ 15.71 (q, J=65 Hz).

HPLC: Daicel Chiralpak IA, hexane/i-PrOH=1000/1, flow rate=0.5 ml/min, UV=230 nm, tR=13.7 min (R), tR=15.3 min (S).

(2-2) Synthesis of (S,S)-i,2-bis(boranato(t-butyl)(t-butylethynyl)phosphino)ethane (1b)

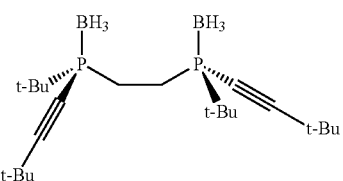

(1b)

The resulting compound 4b was caused to react in the same manner as in Example 1 to give 61 mg (0.15 mmol) of the title compound 1b (>99% ee) in a yield of 73%.

$^1$H-NMR (500 MHz, CDCl$_3$) δ 0.22-0.87 (m, 6H), 1.21-1.25 (d, J=15.1 Hz, 18H), 1.27 (s, 18H), 1.98 (m, 4H).

(2-3) Synthesis of (S,S)-1,2-bis(t-butyl(t-butylethynyl)phosphino)ethane (7b)

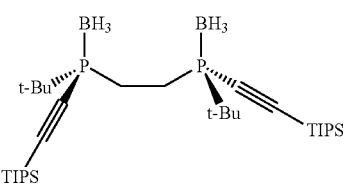

(1c)

The resulting compound 1b was caused to react in the same manner as in Example 1 to give 28 mg (0.075 mmol) of the title compound 7b (>99% ee) in a yield of 94%.

EXAMPLE 3

(3-1) Synthesis of (S)-t-butylmethyl(triisopropylsilylethynyl)phosphine-borane (4c)

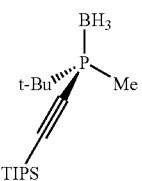

(4c)

The title compound 4c was obtained in the same manner as in Example 1, except for replacing lithium phenylacetylide with lithium triisopropylsilylacetylide. The yield was 1.4 g (4.8 mmol, 86%) with 98% ee.

$^1$H-NMR (400 MHz, CDCl$_3$) δ 0.27-0.73 (m, 3H), 1.09-1.10 (m, 21H), 1.24 (d, J=15.4 Hz, 9H), 1.43 (d, J=10.2 Hz, 3H).

$^{13}$C-NMR (100 MHz, CDCl$_3$) δ 8.45 (d, J=40 Hz), 10.90, 18.43, 24.82 (d, J=3 Hz), 28.62 (d, J=38 Hz), 98.26 (d, J=77 Hz), 113.26 (d, J=3 Hz).

$^{31}$P-NMR (162 MHz, CDCl$_3$) δ 17.48 (q, J=63 Hz).

HPLC: Daicel Chiralpak IA, hexane/i-PrOH=1000/1, flow rate=0.5 ml/min, Uv=230 nm, tR=11.0 min (R), tR=13.6 min (S).

(3-2) Synthesis of (S,S)-1,2-bis(boranato(t-butyl)triisopropylsilylethynyl-phosphino)ethane (1c)

The resulting compound 4c was caused to react in the same manner as in Example 1 to give 1.1 g (1.9 mmol, 78%) of the title compound 1c (>99% ee).

$^1$H-NMR (500 MHz, CDCl$_3$) δ 0.50-0.70 (m, 6H), 1.06-1.14 (m, 42H), 1.27 (d, J=15.3 Hz, 18H), 1.99-2.11 (m, 4H).

(3-3) Synthesis of (S,S)-1,2-bis((t-butyl)triisopropyl-silylethynylphosphino)ethane (7c)

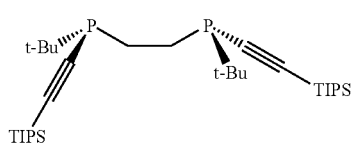

The resulting compound 1c was caused to react in the same manner as in Example 1 to give 44 mg (0.079 mmol, 96%) of the title compound 7c (>99% ee).

EXAMPLE 4

(4-1) Synthesis of (S,S)-1,2-bis(boranato(t-butyl)ethynylphosphino)ethane (1d)

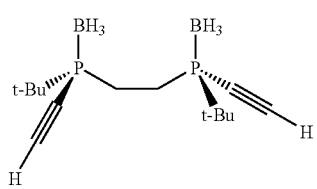

To 60 mg (0.1 mmol) of 1c was added 0.4 ml of a 1.0M solution of tetrabutylammonium fluoride (0.4 mmol) in THF, and the mixture was stirred at room temperature for 6 hours. After the reaction, the reaction was quenched with water. The reaction mixture was extracted three times with ethyl acetate. The organic layers were combined, washed with a saturated sodium chloride aqueous solution, dried over anhydrous sodium sulfate, and filtered. The filtrate was concentrated under reduced pressure, and the residue was purified by silica gel column chromatography (hexane/ethyl acetate=3/1) to give 15 mg (0.052 mmol, 52%, >99% ee) of the titled compound 1d as a white solid.

$^1$H-NMR (400 MHz, CDCl$_3$) δ 0.24-0.90 (m, 6H), 1.29 (d, J=15.7 Hz, 18H), 2.00-2.12 (m, 4H), 3.06 (d, J=7.4 Hz, 2H).

(4-2) Synthesis of (S,S)-1,2-bis((t-butyl)ethynylphosphino)ethane (7d)

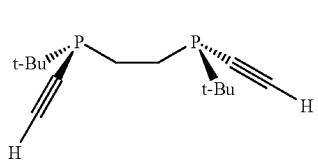

The resulting compound 1d was caused to react in the same manner as in Example 1 to give 19 mg (0.076 mmol, 94%) of the title compound 7d in >99% ee.

EXAMPLE 5

(5-1) Synthesis of (S)-t-butylmethyl(trimethylsilylethynyl)phosphine-borane (X-1)

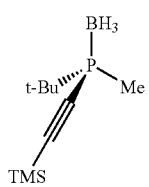

The title compound X-1 was obtained in the same manner as in Example 1, except for replacing lithium phenylacetylide with lithium trimethylsilylacetylide. The yield was 0.92 g (4.3 mmol, 81%) with 99% ee.

$^1$H-NMR (400 MHz, CDCl$_3$) δ 0.22 (s, 3H), 1.23 (d, J=15.4 Hz, 9H), 1.42 (d, J=10.2 Hz, 3H).
$^{13}$C-NMR (125 MHz, CDCl$_3$) δ 0, 8.92 (d, J=40 Hz), 25.45 (d, J=4 Hz), 29.28 (d, J=38 Hz), 96.79 (d, J=77 Hz), 116.66 (d, J=3 Hz).
$^{31}$P-NMR (162 MHz, CDCl$_3$) δ 17.12 (q, J=60 Hz).
[α]22D=−1.59 (c=1.00, CHCl$_3$).
HPLC: Daicel Chiralcel OJ-H, hexane/i-PrOH=99/1, flow rate=0.5 ml/min, UV=230 nm, tR=8.8 min (R), tR=9.7 min (S).

(5-2) Synthesis of (S)-t-butyl(ethynyl)methylphosphine-borane (X-2)

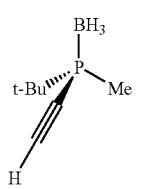

The title compound X-2 was obtained in the same manner as in Example 4, except for replacing 1c with X-1. The yield was 1.2 g (8.6 mmol, 94%) with 99% ee.

(5-2) Synthesis of (S)-t-butyl(1-propynyl)methylphosphine-borane (X-3)

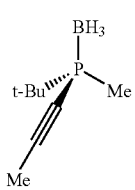

(X-3)

In 1.0 ml of dried THF was dissolved 71 mg (0.5 mmol) of X-2 (99% ee), and 0.38 ml of a 1.6M solution of n-butyl lithium (0.6 mmol) in hexane was added thereto at −78° C. in a nitrogen atmosphere, followed by stirring at that temperature for 5 minutes. To the reaction mixture was further added dropwise 0.16 ml (2.5 mmol) of methyl iodide, followed by stirring at room temperature for 3 hours. After the reaction, the reaction was quenched with water. The reaction mixture was extracted three times with ethyl acetate. The organic layers were combined, washed with a saturated sodium chloride aqueous solution, dried over anhydrous sodium sulfate, and filtered. The filtrate was concentrated under reduced pressure, and the residue was purified by silica gel column chromatography (hexane/ethyl acetate=4/1) to give 76 mg (0.49 mmol, 97%, 99% ee) of the titled compound X-3 as a white solid.

$^1$H-NMR (400 MHz, CDCl$_3$) δ 0.25-0.89 (m, 3H), 1.22 (d, J=15.4 Hz, 9H), 1.40 (d, J=9.9 Hz, 3H), 2.02 (d, J=3.7 Hz, 3H).

(5-4) Synthesis of (S,S)-1,2-bis(boranato(t-butyl)(1-propynyl)phosphino)ethane (1e)

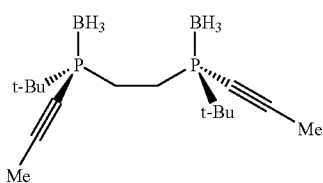

(1e)

In 1.3 ml of dried diethyl ether was dissolved 65 mg (0.42 mmol) of X-3, and 0.46 ml of a 1.0M solution of sec-butyl lithium (0.46 mmol) in hexane was added thereto at −78° C. in a nitrogen atmosphere, followed by aging by stirring at that temperature for 1 hour. To the reaction mixture was added 140 mg (1.0mmol) of copper (II) chloride while vigorously stirring, and the reaction mixture was slowly warmed up to room temperature. Two hours later, the reaction was quenched with a saturated aqueous solution of ammonium chloride. The reaction mixture was extracted three times with ethyl acetate. The organic layers were combined, washed with a saturated sodium chloride aqueous solution, dried over anhydrous sodium sulfate, and filtered. The filtrate was concentrated under reduced pressure. The residue was purified by silica gel column chromatography (hexane/ethyl acetate=4/1) to furnish 20.0 mg (0.063 mmol, 30%) of the title compound 1e as a white solid in >99% ee.

$^1$H-NMR (400 MHz, CDCl$_3$) δ 0.25-0.88 (m, 3H), 1.23 (d, J=15.4 Hz, 18H), 1.42 (d, J=9.8 Hz, 6H), 2.63 (s, 6H).

(5-5) Synthesis of (S,S)-1,2-bis(t-butyl(1-propynyl)phosphino)ethane (7e)

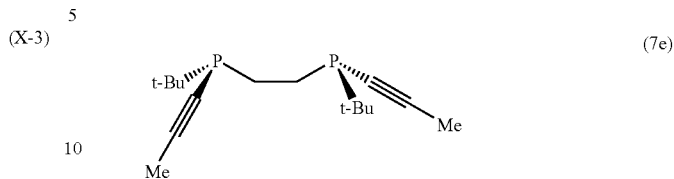

(7e)

The resulting compound 1e was caused to react in the same manner as in Example 1 to afford 24 mg (0.083 mmol, 98%) of the title compound 7e in >99% ee.

EXAMPLE 6

Asymmetric 1,4-Addition of Organic Boronic Acid to Enone using Rhodium Catalyst

A solution of 1.9 mg (5.0 µmol) of [Rh(nbd)$_2$]BF$_4$ and 7.5 µmol of (S,S)-1,2-bis((t-butyl)phenylethynylphosphino)ethane (7a) in 1 ml of dioxane was stirred at 40° C. for 15 minutes in a nitrogen atmosphere. To the reaction solution was added 0.1 ml of a 1.5M aqueous solution of potassium hydroxide (0.15 mmol), followed by stirring for 15 minutes. To the reaction mixture were added 1.0 mmol of allylboronic acid 0.50 mmol of an α,β-unsaturated carbonyl compound, followed by aging while stirring at 40° C. for 2 hours. The reaction was quenched by addition of a saturated sodium hydrogencarbonate aqueous solution. The reaction mixture was extracted with diethyl ether five times. The organic layers were combined, washed with a saturated sodium chloride aqueous solution, and filtered. The filtrate was concentrated under reduced pressure. The residue was purified by preparative TLC on silica gel (hexane/ethyl acetate=3/1). The same procedures were repeated, except for replacing 7a as a ligand with each of 7b, 7c, and 7e. The reaction results are shown in Table 1 below.

TABLE 1

| Run No. | Ligand | Enone | R | Time (hr) | Yield (%)*[1] | ee (%) (config.) |
|---|---|---|---|---|---|---|
| 1 | 7a | 1 | Ph | 2 | 93 | 99 (R) |
| 2 | 7a | 1 | 4-MeOC$_6$H$_4$ | 2 | 99 | 98 (R) |
| 3 | 7a | 1 | 4-CF$_3$C$_6$H$_4$ | 2 | 96 | 96 (R) |
| 4*[2] | 7a | 2 | Ph | 6 | 89 | 92 (R) |
| 5 | 7a | 3 | Ph | 2 | 90 | 91 (R) |
| 6 | 7a | 4 | Ph | 2 | 91 | 97 (+) |
| 7*[3] | 7b | 1 | Ph | 2 | 94 | 46 (R) |
| 8*[4] | 7c | 1 | Ph | 12 | 64 | 68 (R) |

TABLE 1-continued $$\text{cyclic enone} + RB(OH)_2 \xrightarrow[\text{KOH (50 mol \%)}]{\text{[Rh(nbd)}_2]\text{BF}_4/\text{ligand}\ (1\ \text{mol \%})}_{\text{dioxane/H}_2\text{O}(10/1),\ 40\ \text{deg.}} \text{product}$$

| Run No. | Ligand | Enone | R | Time (hr) | Yield (%)*1 | ee (%) (config.) |
|---|---|---|---|---|---|---|
| 9 | 7e | 1 | Ph | 1 | 93 | 99 (R) |
| 10 | 7e | 1 | 4-CF$_3$C$_6$H$_4$ | 1 | 94 | 99 (R) |

Note:
*1: isolation yield
*2: reaction temperature: 45° C.
*3: reaction temperature: 50° C.
*4: reaction temperature: 70° C.
Enone 1: 2-cyclohexenone
Enone 2: 2-cycloheptenone
Enone 3: 2-cyclopentenone
Enone 4: (E)-5-methyl-3-hexen-2-one

EXAMPLE 7

Asymmetric Hydrogenation using Rhodium Catalyst

In a 50 ml container for hydrogenation (autoclave) was put 0.5 mmol of a substrate. The container was connected to a hydrogen cylinder via a stainless steel pipe. The container was evacuated and filled with 1 atm hydrogen (99.9999%, from Nippon Sanso). A solution of 1.9 mg (5.0 μmol) of [Rh(nbd)$_2$]BF$_4$ and 7.5 μmol of (S,S)-1,2-bis((t-butyl)phenylethynylphosphino)-ethane (7a) in 1 ml of deaerated methanol was syringed into the container, followed by elevating the hydrogen pressure to 3 atm. The reaction mixture was concentrated, and the residue was purified by flash chromatography on silica gel using ethyl acetate as an eluate. The same procedures were repeated, except for replacing 7a as a ligand with each of 7b, 7c, 7d, and 7e. The reaction results obtained are shown in Table 2.

TABLE 2

$$\text{Ph-CH=C(NHCOMe)(CO}_2\text{Me)} \xrightarrow[\text{H}_2\ (1\ \text{atm}),\ \text{MeOH},\ 1\ \text{h}]{\text{[Rh(nbd)}_2]\text{BF}_4/\text{ligand}\ (1\ \text{mol \%})} \text{Ph-CH}_2\text{-CH(NHCOMe)(CO}_2\text{Me)}$$

| Run No. | Ligand | Yield (%) | ee (%) (config.) |
|---|---|---|---|
| 1 | 7a | 100 | 92 (R) |
| 2 | 7b | 100 | 90 (R) |
| 3 | 7c | 100 | 88 (R) |
| 4 | 7d | 100 | 99.5 (R) |
| 5 | 7e | 100 | 99.6 (R) |

EXAMPLE 8

Ring Opening with Alkylation of Oxabenzonorbornadiene Derivative

A solution of 1.1 mg (4.0 μmol) of PdCl$_2$(cod) and 6 μmol of (S,S)-1,2-bis(t-butyl)ethynylphosphino)ethane (7d) in 1 ml of dichloromethane was stirred at 40° C. for 15 minutes in a nitrogen atmosphere. To the reaction mixture was added a solution of 58 mg (0.4 mmol) of oxabenzonorbornadiene in 3 ml of dichloromethane. Subsequently, 0.6 ml of a 1.0M hexane solution of dimethyl zinc (0.6 mmol) was added thereto, followed by aging while stirring the reaction mixture at room temperature until completion of the reaction. After the reaction, a few drops of water were added to quench the reaction. The reaction mixture was passed through a short column of Celite and then concentrated. The residue was purified by preparative TLC (hexane/ethyl acetate). The same procedures were conducted, except for replacing 7d as a ligand with each of 7a, 7b, 7c, and 7e. The reaction results are shown in Table 3.

TABLE 3

$$\text{oxabenzonorbornadiene} \xrightarrow[\text{CH}_2\text{Cl}_2,\ \text{rt},\ 1.5\ \text{h}]{R^2_2\text{Zn},\ \text{PdCl}_2(\text{cod})/\text{ligand}\ (2\ \text{mol \%})} \text{ring-opened product}$$

| Run No. | Ligand | R$^1$ | R$^2$ | Yield*1 (%) | ee (%) (config.) |
|---|---|---|---|---|---|
| 1 | 7a | H | Me | 92 | 96 (1S,2S) |
| 2*2 | 7a | H | Et | 93 | 96 (1S,2S) |
| 3 | 7a | OMe | Me | 87 | 88 (1S,2S) |
| 4 | 7b | H | Me | 90 | 90 (1S,2S) |
| 5 | 7c | H | Me | 92 | 96 (1S,2S) |
| 6 | 7d | H | Me | 93 | 99.9 (1S,2S) |
| 7*2 | 7d | H | Et | 90 | 99.9 (1S,2S) |
| 8 | 7e | H | Me | 91 | 99.8 (1S,2S) |

Note:
*1: isolation yield
*2: reaction time: 6 hours

As fully described above, an optically-active bis(alkynylphosphino)ethane derivative obtained from the compound of the present invention serves as a ligand to provide an asymmetric catalyst for catalytic asymmetric synthesis reactions exhibiting high selectivity and catalyst activity.

What is claimed is:

1. An optically-active bis(alkynylphosphino)ethane-borane compound represented by formula (1):

$$R^1-\!\!\equiv\!\!-\underset{R^3}{\overset{BH_3}{P^*}}-CH_2CH_2-\underset{R^3}{\overset{BH_3}{P^*}}-\!\!\equiv\!\!-R^2 \qquad (1)$$

wherein R$^1$ and R$^2$, which may be the same or different, each represent an alkyl group, a phenyl group, an alkylsilyl group or a hydrogen atom; R$^3$ represents a branched alkyl group, an alicyclic hydrocarbon group or an aromatic hydrocarbon group; and the asterisk * indicates an optically-active site.

2. The compound of claim 1, wherein R$^1$ and R$^2$ are the same and each represent a methyl group, a t-butyl group, a phenyl group, a triisopropylsilyl group or a hydrogen atom.

3. The compound of claim 1, wherein $R^3$ is a t-butyl group.

4. A process for producing the optically-active bis(alkynylphosphino)ethane-borane compound of claim 1, comprising the steps of:

brominating a t-butylmethylphosphine-borane represented by formula (2):

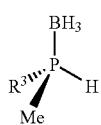
(2)

wherein $R^3$ is as defined above, to obtain a t-butylmethylbromophosphine-borane represented by formula (3):

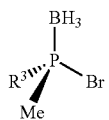
(3)

wherein $R^3$ is as defined above, causing an alkynyl lithium to react on the compound of formula (3) to obtain a configuration-inverted compound represented by formula (4):

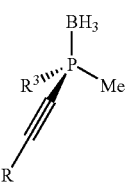
(4)

wherein R represents $R^1$ or $R^2$; and $R^3$ is as defined above, and deprotonating the compound of formula (4), followed by oxidative coupling.

5. The compound of claim 2, wherein $R^3$ is a t-butyl group.

* * * * *